(12) United States Patent
Korten et al.

(10) Patent No.: US 10,500,020 B2
(45) Date of Patent: Dec. 10, 2019

(54) DEVICE FOR POWDER BASED ADDITIVE MATERIAL MANUFACTURING OF DENTAL APPLIANCES

(71) Applicant: 3M INNOVATIVE PROPERTIES COMPANY, St. Paul, MN (US)

(72) Inventors: Malte Korten, Moorenweis (DE); Rainer K. Dittmann, München (DE); Hans R. Schnagl, Jengen (DE)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 273 days.

(21) Appl. No.: 15/315,624

(22) PCT Filed: May 27, 2015

(86) PCT No.: PCT/US2015/032627
§ 371 (c)(1),
(2) Date: Dec. 1, 2016

(87) PCT Pub. No.: WO2015/187422
PCT Pub. Date: Dec. 10, 2015

(65) Prior Publication Data
US 2017/0112601 A1    Apr. 27, 2017

(30) Foreign Application Priority Data
Jun. 6, 2014    (EP) ..................... 14171448

(51) Int. Cl.
| | |
|---|---|
| *B29C 64/20* | (2017.01) |
| *A61C 13/00* | (2006.01) |
| *B33Y 30/00* | (2015.01) |
| *B33Y 10/00* | (2015.01) |
| *B33Y 80/00* | (2015.01) |

(Continued)

(52) U.S. Cl.
CPC ............ *A61C 13/0013* (2013.01); *A61C 5/77* (2017.02); *A61C 13/0022* (2013.01);
(Continued)

(58) Field of Classification Search
CPC ....... B29C 64/153; B28B 1/001; B22F 3/105; B65D 83/06; A61C 5/77
See application file for complete search history.

(56) References Cited

U.S. PATENT DOCUMENTS

| | | |
|---|---|---|
| 4,684,862 A | 8/1987 | Rohrle |
| 5,151,044 A | 9/1992 | Rotsaert |

(Continued)

FOREIGN PATENT DOCUMENTS

| | | |
|---|---|---|
| CN | 2767104 | 3/2006 |
| DE | 19944130 | 4/2001 |

(Continued)

OTHER PUBLICATIONS

International Search Report for PCT International Application No. PCT/US2015/032627, dated Aug. 12, 2015, 4 pages.

*Primary Examiner* — Jacob T Minskey
*Assistant Examiner* — Cedrick S Williams
(74) *Attorney, Agent, or Firm* — 3M Innovative Properties Company

(57) ABSTRACT

A device for powder based additive material manufacturing of dental appliances. The device has a recoater (10) for providing a powder layer to a build area. The recoater (10) has a slide (11) and is adapted for dispensing of the powder to the build area. The recoater (10) has further at least two powder supplies for individually supplying a first and a second powder on the slide (11) and a powder transport section in which the first and second powder are brought in touch with each other for at least partially merging. The invention is advantageous in that it allows providing dental blanks having color gradients in all three dimensions.

17 Claims, 4 Drawing Sheets

(51) Int. Cl.
  *A61C 5/77* (2017.01)
  *A61C 13/08* (2006.01)
  *B28B 1/00* (2006.01)
  *B29C 64/165* (2017.01)

(52) U.S. Cl.
  CPC ............ *A61C 13/082* (2013.01); *B28B 1/001* (2013.01); *B29C 64/20* (2017.08); *B33Y 10/00* (2014.12); *B33Y 30/00* (2014.12); *B33Y 80/00* (2014.12); *A61C 13/0021* (2013.01); *B29C 64/165* (2017.08)

(56) References Cited

U.S. PATENT DOCUMENTS

| | | | |
|---|---|---|---|
| 5,837,960 A * | 11/1998 | Lewis | B23K 26/34 219/121.63 |
| 7,673,581 B2 | 3/2010 | Ueberschär | |
| 8,173,562 B2 | 5/2012 | Holand | |
| 8,943,964 B2 | 2/2015 | Foerch | |
| 2009/0004380 A1 | 1/2009 | Hochsmann | |
| 2009/0014086 A1 | 1/2009 | MacMichael | |
| 2012/0266397 A1* | 10/2012 | Iwahori | A46B 15/0006 15/22.1 |
| 2013/0108726 A1 | 5/2013 | Uckelmann | |
| 2014/0377117 A1* | 12/2014 | Herrmann | B65D 83/06 419/1 |

FOREIGN PATENT DOCUMENTS

| | | | |
|---|---|---|---|
| WO | WO 2002-09612 | 2/2002 | |
| WO | WO 2008-083358 | 7/2008 | |
| WO | WO 2012-078533 | 6/2012 | |
| WO | WO 2013-095968 | 6/2013 | |
| WO | WO 2014-071968 | 5/2014 | |
| WO | WO-2014071968 A1 * | 5/2014 | ............ B22F 1/0085 |

* cited by examiner

DEVICE FOR POWDER BASED ADDITIVE MATERIAL MANUFACTURING OF DENTAL APPLIANCES

FIELD OF THE INVENTION

The invention relates to a device for powder based additive material manufacturing of dental appliances, and in particular to a device which allows horizontal layering of differently colored (or differently characterized) powder materials with a smooth transition of the materials into one another.

BACKGROUND ART

In the field of dentistry, the restoration of a patient's tooth or teeth generally includes the replacement of the natural tooth substance by an artificial substance. For larger restorations, pre-finished dental restorations or prostheses are commonly used to replace the tooth or teeth or at least part of those.

Ceramic materials are widely used for making high-quality dental restorations because of their good physical, aesthetic and biological properties. These restorations are often manufactured in automated processes, which typically include the use of computer-aided design (CAD) techniques and manufacturing by Computer Numerical Controlled (CNC) machines.

In the manufacturing of dental restorations various automated processes are established in practice. One common method includes the preparation of standardized blanks that subsequently can be used to machine individual dental restorations or precursors thereof by removing material from the blank. Except for providing such blank at a sufficient size suiting for a multiplicity of different types of dental restorations, the shape of the blank typically does not correlate with any individual shape of a tooth in patient's mouth.

While such processes provide various advantages meanwhile so-called build-up processes have been proposed for making dental restorations. Such a build-up process typically allows building up an individual dental restoration in substantially its desired individual shape, generally by subsequently adding material to create that shape instead of providing an oversized standardized blank from which material is removed in a subsequent process. For example WO 2012/078533 describes such a build-up process and corresponding devices for making a dental restoration from a powdery ceramic material.

Restorations manufactured by use of automated processes are often finished, for example by a dental technician, by coloring and/or glazing to make the restoration pleasantly fit with other teeth in the patient's mouth. Co-pending international patent application PCT/US2012/068724 further describes a method and system for providing a dental restoration with an individual color within an automated manufacturing process.

Although existing processes for making dental restoration are advantageous in different respects there is a general desire to provide a process for making individual or customized dental restorations at a high degree of automation, maximized quality and minimized costs.

SUMMARY OF THE INVENTION

In one aspect the invention relates to a device for powder based additive material manufacturing of dental appliances. The device comprises a build area and a recoater for providing a powder layer to the build area. Further the recoater comprises a slide and is adapted for dispensing of the powder to the build area. The recoater has at least two powder supplies for preferably separately storing and individually supplying a first and a second powder on the slide. Further the recoater has a powder transport section in which the first and second powder are brought in touch with each other for at least partially merging. Each powder supply has an outlet. The powder supply outlets are arranged adjacent each other.

Preferably the device is configured such that the force of gravity is utilized in addition to mechanical forces generated by the device for dispensing of the powder. This means that the powder supplies are preferably arranged geographically above the build area so that the vertical flow of the powder can be supported by the force of gravity.

For the purpose of the present specification the term "vertical" refers to a dimension which is arranged in a dimension of the natural forth of gravity on the earth and the term "horizontal" refers to a dimension perpendicular thereto. Further the deposition of the powder in the build area is preferably based on generating powder layers in an opposite direction of a direction toward the center of the earth. In this regard a lower layer of a blank or a precursor of that blank is a layer which during generation of that blank or blank precursor is oriented toward the center of the earth and an upper layer is a layer in the same blank or blank precursor but farther away from the center of the earth. Lateral layers for the purpose of the present specification are layers in dimensions perpendicular to the vertical dimension.

The invention is advantageous in that it allows providing dental blanks having color gradients in all three dimensions. In particular the invention allows smooth color transitions within the dental blanks not only, as some prior art blanks, in a vertical dimension but also in one or both lateral dimensions. Further the invention allows for relatively precisely controlling at least the color transition in the lateral dimensions. In general the invention helps providing dental restorations which pleasantly resemble natural teeth and which can be made relatively inexpensive, for example by use of automated milling and/or grinding techniques.

In one embodiment the powder supply outlets are arranged directly side-by-side. Thus, amounts of the first and second powder released from the outlets fall onto the slide side-by-side and deposit on the slide touching and/or overlapping each other.

In one embodiment the slide has a (preferably generally planar) powder receiving surface terminating at one end in a dispensing edge. The device may be adapted such that a vibration of the slide supports powder deposited on the powder receiving surface to slide toward the dispensing edge. The device may for example have a motor for driving a crank mechanism. The crank mechanism may have a link which rotates motor-driven on a circular path eccentrically to the motor axis. The crank mechanism may further have a crank shaft driven via the link. Thus the crank shaft can be used to move the slide translational in an oscillating fashion and thus cause the vibration to the slide. Further the slide may be arranged such that the powder receiving surface has a slope with respect to a horizontal plane. That slope preferably extends downward toward the dispensing edge.

In one embodiment the powder receiving surface further forms the powder transport section. The powder transport section may further comprise a first partial powder transport section arranged adjacent the powder supplies and a second partial powder transport section formed by the powder receiving surface of the slide. The first partial powder transport section in this embodiment is preferably not formed by the powder receiving surface and arranged apart from the slide. In this case a pre-merging of the powders may be provided before the powders fall on the powder receiving surface of the slide.

In a further embodiment outlets of the individual powder supplies are arranged essentially parallel to the powder receiving surface. The outlets of the individual powder supplies are preferably arranged essentially in one horizontal plane. In particular the lower margins of the outlets of the individual powder supplies are arranged essentially in one horizontal plane.

The device is preferably adapted such that the recoater and the build area are movable relative to each other along an X-axis. The X-axis extends preferably generally horizontal. The dispensing edge further preferably extends along a generally horizontal Y-axis perpendicular to the X-axis.

The outlets of the powder supplies further may be arranged along a first dimension generally parallel to the dispensing edge. Preferably that first dimension extends parallel to the Y-axis. Further the outlets of the powder supplies may be arranged along a second dimension transverse to the dispensing edge. Preferably that second dimension extends parallel to the X-axis. The outlets of the powder supplies further may be arranged along an angle between the first and second dimension, for example angularly inclined relative to the X-axis and the Y-axis.

Furthermore the outlets of the powder supplies may be juxtaposed along a generally regular zigzag line whose (imaginary) centerline extends generally parallel to the dispensing edge or parallel to the Y-axis. This allows for overlapped deposition of two or more individual powder also without the aid of vibrations.

Preferably each powder supply has one outlet for the powder contained in the respective powder supply. The powder supply outlets are preferably arranged adjacent each other, for example side by side in one plane.

In one embodiment the build area has a build platform exhibiting a generally planar build surface. The build surface is preferably generally horizontal in both dimensions in which it extends. The dispensing edge is preferably arranged generally parallel to the build surface. Further the build platform and the slide are movable relative to each other in a dimension parallel to the build surface and a dimension perpendicular thereof, namely in a dimension of the X-axis. The dispensing edge is preferably spaced relative to build surface. Powder may be dispensed on the build surface during a movement of the recoater relative to the build surface in a dispensing direction along the X-axis. The dispensed powder is preferably leveled by the recoater being retracted in a retraction direction opposite of the dispensing direction.

In a further embodiment at least one or each of the powder supplies comprises a container for holding an amount of powder. The container may extend generally vertically and may have a bottom end comprising the outlet in the form of an opening in the container. The container or containers may be detachably attached to the device. Further each opening may extend in a dimension generally horizontally through a wall of the container.

In a further embodiment at least two of the powder supplies each comprise a powder. The color of the powder in one of the powder supplies is preferably different than the color of the powder in the other powder supply. Further the translucency of the powder in one of the powder supplies is preferably different than the translucency of the powder in the other powder supply. In this regard the term "color of the powder" and the term "translucency of the powder" refer to characteristics of the material the powder is formed from. Accordingly the color and translucency of the powder preferably refers to characteristics of the material at its fully sintered stage although the lose powder in a bulk may have different characteristics.

In one embodiment the powder contains one or more elements to obtain optical effects like color and fluorescence selected from among Fe, Tb, Er, Mn, Bi, Th, Pr, Mn and combinations thereof. Preferably different powders in different powder supplies contain different and/or different amounts of those elements.

In a further embodiment the powder supplies and the slide are mechanically coupled so as to enable transmission of vibrations between the slide and the powder supplies. This supports flow of the powders out of the powder supplies as well as the partial merging the powders, for example on.

In one embodiment the recoater comprises a box having a first, second, third and fourth outer side wall each extending generally vertical. The box further may have a bottom wall which forms the slide. The slide is preferably in connection with the second, third, and fourth side wall. The first side wall and the bottom wall are preferably spaced from each other. The box further comprises at least one separation wall extending between the first side wall and the opposite second side wall. The separation wall(s) is/are in connection with the bottom wall. Thus one box forming two or more powder supplies is provided. The outlets of the powder supplies are preferably formed by the space between the front and bottom wall and delimited by the separation wall(s). A set of boxes may be provided having different pre-determined selections of different powder materials, for example differently colored and/or powder materials having different translucencies and/or mechanical properties.

In a further aspect the invention relates to a method of making a dental appliance based on powder based additive material manufacturing. The method comprises the steps of:
  providing at least two different powders on a vibratory slide for vibration-supported dispensing of the powder to a build platform in the form of side by side powder tracks,
  vibrating the slide so as to cause the powders to flow in side by side tracks toward a dispensing edge of the slide, wherein the dispensing edge is arranged transverse to the dimension along which the powder tracks extend.

The at least two different powders may be provided on the vibratory slide in a side by side and partially overlapping fashion.

In one embodiment the powder is formed from a zirconia composition comprising:
  Zr oxide calculated as ZrO2: from about 80 to about 97 wt.-%,
  Al oxide calculated as Al2O3: from about 0 to about 0.15 wt.-%,
  Y oxide oxide calculated as Y2O3: from about 1 to about 10 wt.-%,
  Bi oxide calculated as Bi2O3: from about 0 to about 0.20 wt.-%,
  Tb oxide calculated as Tb2O3: from about 0 to about 0.8 wt.-%,
and optionally one or more of the following oxides:
  Fe oxide calculated as Fe2O3: from about 0 wt.-% to about 0.15 wt.-%
  Er oxide calculated as Er2O3: from about 0 wt.-% to about 1.0 wt.-%, Mn oxide calculated as MnO2: from about 0 wt.-% to about 0.03 wt.-%, wt.-% (percent by weight) with respect to the weight of the zirconia material.

The average grain size of the powder may be less than about 100 nm.

If desired, the average grain size can be determined with the Line Intercept Analysis. FESEM micrographs with 70,000 times magnification are used for grain size measurement. Three or four micrographs taken from different areas of the sintered body are used for each sample. Ten horizontal lines, which are spaced at roughly equal intervals across the height of each micrograph, are drawn. The numbers of grain boundary intercepts observed on each line are counted and used to calculate the average distance between intercepts. The average distance for each line is multiplied by 1.56 to determine the grain size and this value is averaged over all the lines for all micrographs of each sample.

BRIEF DESCRIPTION OF THE FIGURES

FIG. 1A is a detail view relating to the device of FIG. 1;

DETAILED DESCRIPTION OF THE INVENTION

Figure 1:
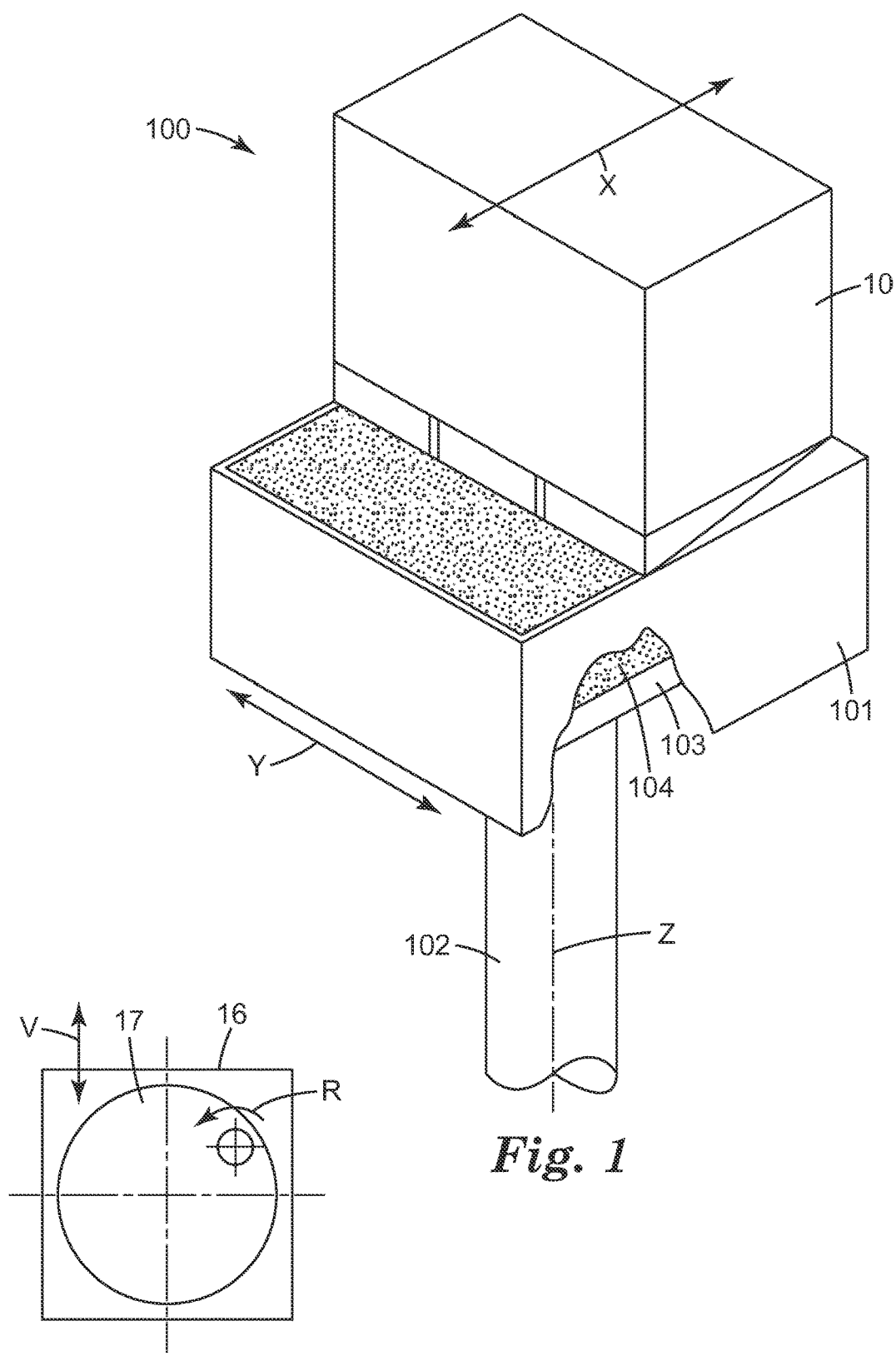
FIG. 1 is a perspective view of a device according to an embodiment of the invention.

FIG. 1 schematically illustrates a device 100 for powder based additive material manufacturing. A build box 101 for receiving the powder is removably placed in the device 100. A lift 102 which is movable along a Z axis carries a build platform 103 which serves as a support for the powder received in the build box 101. Typically the build platform 103 is positioned such that a space is left between the top of the build box and the platform 103 or, if powder is deposited already on the platform 103, between the top of the build box and the upper surface powder. The device 100 is preferably adapted such that the lift 102 is movable to any desired position to control the dimension of that space, and thereby to control the thickness of the layer of powder received in that space.

The device 100 further comprises a recoater 10 for providing powder into the build box 101. In more general, although the example uses a build box, the recoater 10 is adapted to provide powder to a build area of the device 100. Such a build area may, for example, be formed by the build platform 103 only (without presence of any build box). In that case the build platform may alternatively be arranged at a fixed position on the Z axis in the device and the recoater 10 may be movable relative to the platform along the Z axis, or vice versa. The recoater 10 is further movable along an X axis that is perpendicular to the Z axis. The X axis further is arranged generally parallel to a build surface 104 of the build platform 103. It is further possible that the build platform 103 is movable along the X axis, whereas the recoater 10 is arranged at a fixed position on the X axis in the device. In summary therefore the recoater 10 and the build platform 103 are movable relative to each other in a dimension of the Z axis and, preferably independently therefrom, in a dimension of the X axis.

For building an object by additive material manufacturing, the recoater 10 is used to provide a layer of powder on the build platform 103 in that the recoater 10 and the platform 103 are positioned along the Z axis at a predetermined space relative to each other. Based thereon powder is dispensed on the platform 103 by the recoater 10 while the recoater 10 moves along the X axis. The speed of the movement along the X axis is for example about 0.5 m/s. Typically the recoater 10 is moved in a first direction of the X axis to dispense the powder first, and retracted in the opposite second direction of the X axis after. Thereby the recoater levels the powder dispensed to the platform 103 to a height approximately corresponding to the predetermined space between the platform 103 and the recoater 10. Thus a first powder layer is created on the platform 103. Further powder layers can be created by the same steps, but with respective further layers being provided on the respective top most previous layer instead of on the platform 103 directly. The skilled person will recognize that a recoater may be adapted to provide powder into the platform upon movement in both directions of the X axis, for example two recoaters 10 may be used arranged in opposite directions. To create an object in the form of a solid structure, each time a powder layer is provided and before a next powder layer is provided on top, a liquid, for example a binder and/or reactant, is typically dispensed on the powder layer in the form of a two-dimensional pattern. The liquid typically penetrates through the individual powder layer and connects to the respective pattern, if present, beneath that layer. The device 100 therefore may further have a liquid dispenser (not illustrated) which is movable, for example in a computer numerically controlled (CNC) manner, along the X axis and further along a Y axis. Such liquid dispenser may have a nozzle which is arranged above the platform 103. Depending on the type of liquid and powder used, the combination of powder and liquid or the liquid alone is allowed or caused to harden, thus forming a coherent solid structure extending across several powder layers. Excess powder may be removed to obtain the built object.

In the example however, no liquid may be dispensed but just powder layers may be built within the build box 101. The build box 101 may subsequently be used to compress the powder therein to form a coherent block or blank of powder. The compression may be performed by axial pressing at pressures between about 100 MPa and about 300 MPa if—as in the example—a zirconia material is for example used, so that the powder forms a coherent blank. The skilled person will recognize that axial pressing may be performed by uniaxial or biaxial pressing, depending on the equipment available and the desired structure of the pressed blank. For the purpose of the present invention both, uniaxial and biaxial pressing may be used. The compression typically causes the powder particles to adhere but with leaving spaces between non adherent areas. This state of the blank is also referred to as "green density" in the art of ceramics. An axial pressing step may also be followed by an isostatic pressing step at pressures between about 150 MPa and about 250 MPa. If a subsequent axial and isostatic pressing process is used, the axial pressing pressures may be as low as to provide the compressed blank with just sufficient coherence as to allow it to be transferred into the isostatic press without causing it falling apart. In the example the blank may be pre-sintered at temperatures of between 700° C. and 1200° C. Thereby any binders eventually present in the powder are also removed. At this stage the blank has typically still a somewhat porous structure. A so prepared blank may be machined and finally sintered to full density at temperatures of between about 1300° C. to about 1600° C. to form a dental appliance. The skilled person will recognize that the compression forces and temperatures may vary depending on the powder material(s), including binders, used.

Figure 2:
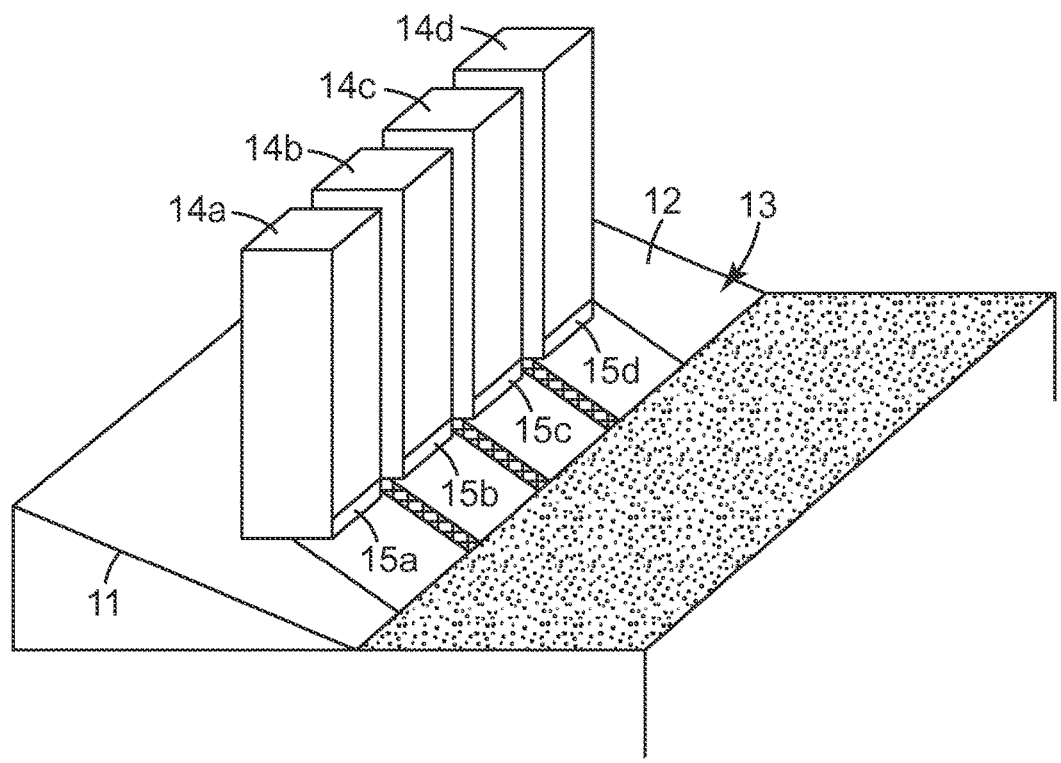
FIG. 2 is a perspective view of a device according to a further embodiment of the invention.

FIG. 2 shows a further embodiment of a recoater 10 in more detail. The recoater 10 comprises a vibratory slide 11 for vibration-supported dispensing of the powder to the build area. The vibratory slide 11 is has a generally planar powder receiving surface 12 terminating at one end in a dispensing edge 13. The slide 11 is arranged such that the powder receiving surface 12 in one dimension is inclined with respect to a horizontal plane. In particular the slide 11 is arranged such that the powder receiving surface 12 forms a downward slope toward the dispensing edge 13. Thus a powder received on the powder receiving surface 12 tends to flow toward the dispensing edge 13 by force of gravity. The slope may me adjustable although it is fixed in the example. The recoater 10 further has a vibration generator (an example of which is schematically illustrated in FIG. 1A). The vibration generator may, for example, have a motor driven crank drive 16 which converts a rotation R into vibrations V. The crank drive 16 is based on an eccentrically rotationally driven shaft 17. The rotation axis of the shaft 17 thus is offset from the rotation axis about which the shaft 17 is rotated. Accordingly the velocity of the vibration generated by the vibration generator is determined by the offset and the frequency at which the shaft is rotated. The vibration generator is connected to the slide to induce the slide 11 and thus the powder to vibrate. The frequency is adjustable between 0 and 4000 rpm and the eccentricity measured at the dispensing edge 13 is about 1 mm (measured based on the extreme positions of oscillating translational movement along a dimension parallel to the X axis). The vibration facilitates the flow of the powder and causes any powder deposited on the slide and exposed to such vibrations to flow toward the dispensing edge, where it falls off the slide toward the build area. It is noted that in the present example the oscillating translational vibrations are applied to the slide in a dimension of the X axis, whereas in another example the vibrations may be applied to the slide additionally or only in a dimension of the Y axis.

In the example a plurality of powder supplies 14a, 14b, 14c, 14d are arranged above the slide 11 for individually supplying a powder from each of the powder supplies 14a, 14b, 14c, 14d. The powder supplies 14a, 14b, 14c, 14d and outlets 15a, 15b, 15c, 15d of those further are arranged generally parallel to the dispensing edge. Thus powder dispensed from the outlets 15a, 15b, 15c, 15d of the powder supplies 14a, 14b, 14c, 14d is deposited side-by-side along a dimension parallel to the dispensing edge 13. While it is possible to supply the same type of powder from each of the powder supplies 14a, 14b, 14c, 14d, according the invention preferably at least a first and a second powder of different types are supplied. For example the first powder may be supplied from powder supplies 14a and 14c, whereas the second powder may be supplied from powder supplies 14b and 14d. Accordingly in operation of the recoater 10 the powder supplies 14a, 14b, 14c, 14d may continuously supply the first and second powder (or four different powders) on the slide 11, where the first and second powder (or the four different powders) run in alternately side-by-side arranged tracks toward the dispensing edge 13. It has been found that the powder tracks do not only run toward the dispensing 13 edge but further spread as they run toward the dispensing edge 13. Therefore the tracks partially merge into one another at their margins laterally to direction of flow as they run toward the dispensing edge 13. The extent of the merging of the powder can be controlled by the velocity of the vibrations, the length of the travel of the powder between the powder supplies 14a, 14b, 14c, 14d and the dispensing edge 13, and the slope of the slide. In one example the length of travel is between about 2 mm and about 30 mm, and the slope is between about $1/10$ mm/mm and $10/10$ mm/mm length. The skilled person will recognize that further each or only some of the powder supplies 14a, 14b, 14c, 14d may supply a different type of powder, as appropriate.

Figure 3:
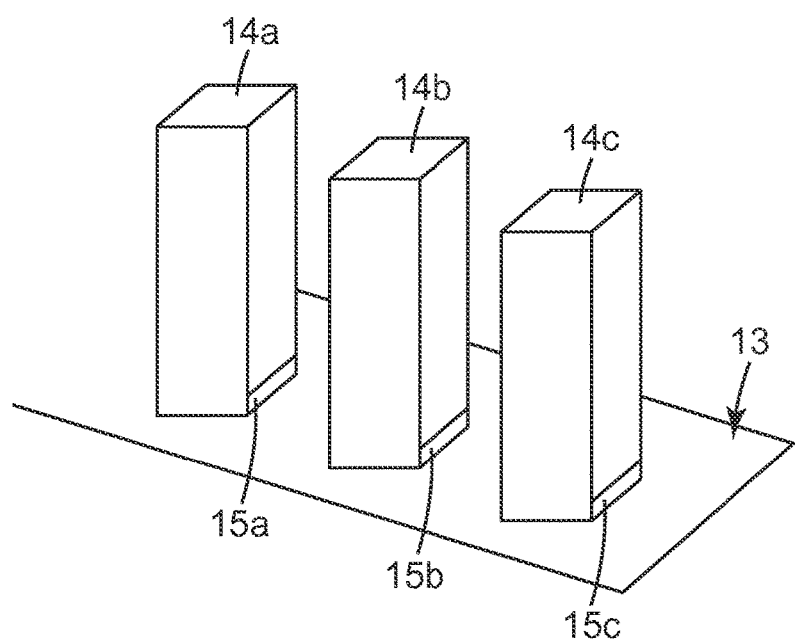
FIG. 3 is a perspective view of a device according to another embodiment of the invention.

In a further example illustrated in FIG. 3 powder supplies 14a, 14b, 14c and outlets 15a, 15b, 15c of those are arranged in a dimension transverse to the dispensing edge. Therefore powder supplied by the powder supply 14a is overlaid by a further powder supplied by the powder supply 14b and powder supply 14c overlays the two powder layers from powder supplies 14a, 14b as the powders run toward the dispensing edge 13. Thus the powders can be premixed or merged by dispensing the powders overlapped with each other.

In a further example (not illustrated) powder supplies 14a, 14b, 14c and outlets 15a, 15b, 15c of those are arranged in a dimension transverse to the dispensing edge 13 and in addition laterally offset thereto. Such a configuration allows for dispensing the individual powders in a partially overlapped manner and to cause a further partial merging of powder the powder tracks created thereby via vibration.

Preferably the different powder types differentiate by color, for example by different tooth colors, different translucencies, different mechanical properties and combinations thereof. In a preferred embodiment the different powder types differentiate by color. Accordingly the invention allows building up a dental blank having at least two layers of a first tooth color and a different second tooth color, wherein the at least two layers merge into one another into a transition layer having at least a third tooth color. Such transition layer typically forms a color gradient extending within a range from the first tooth color via the third tooth color to the second tooth color. The third tooth color thereby is formed by a mixture from the first and second tooth color. Preferably the term "tooth color" refers to the color of the blank or the dental restoration at the finally sintered stage. The color of the powder used to build up the blank may vary therefrom and may obtain the final tooth color only after sintering. Typical tooth colors as useful for the present invention may comprise the colors B1, A1, B2, D2, A2, C1, C2, D4, A3, D3, B3, A3.5, B4, C3, A4, C4 according to the VITA Classical Shade Guide of the company VITA Zahnfabrik, Germany.

Figure 4:
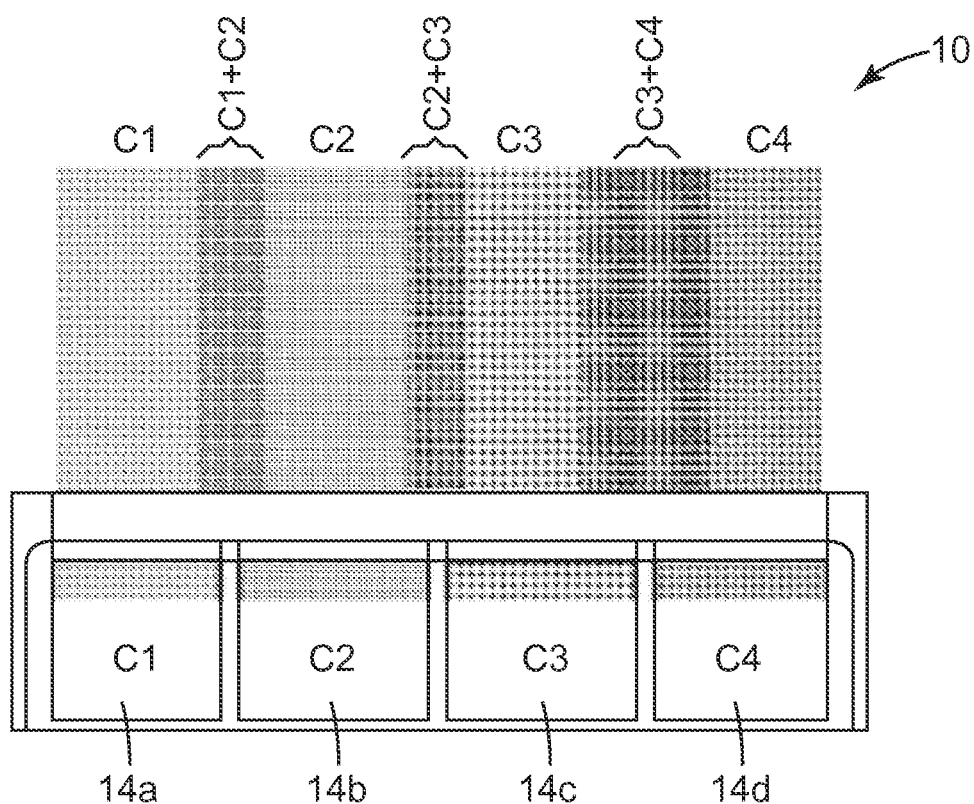
FIG. 4 is a top view of a device according to an embodiment of the invention.

FIG. 4 schematically shows in a top view an embodiment of a recoater 10 having four powder supplies 14a, 14b, 14c, 14d provided with differently colored powder materials C1, C2, C3, C4, respectively. The powder materials C1, C2, C3, C4 flow in the form of side-by-side tracks in a direction parallel to an X axis as shown. The powder flow is supported by vibration as described. The powder tracks partially merge into one another at their lateral margins and thus form transition zones composed of powders C1+C2, C2+C3 and C3+C4. Accordingly a powder layer can be provided to a build up area (not shown) which exhibits the colors C1, C2, C3, C4 and color grades from C1 to C2, C2 to C3 and C3 to C4. Due to the transition zones in the powder and the resulting color grades a smooth transition between the individual colors is achieved. This is advantageous in that it allows providing a dental restoration which relatively closely resembles color transitions of natural teeth.

EXAMPLE

A recoater of the invention was used to build up a multi-colored blank. For the purpose of clearly demonstrating the transitions between the different colors, powders of very different colors have been used. In particular a relatively bright powder and a relatively dark powder were alternately arranged relative to each other in one layer.

Figure 5:
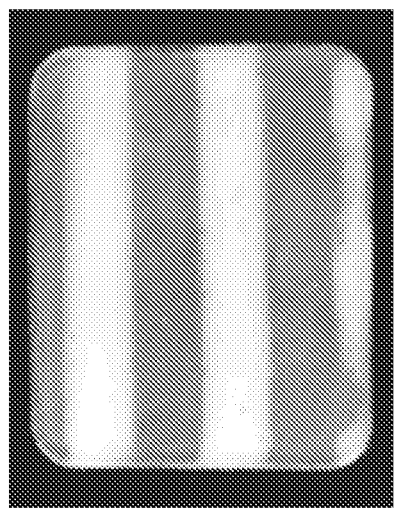
FIGS. 5, 6 are top views of samples obtained using a device according to an embodiment of the invention.

The recoater was operated without applying vibrations to the powder. Several of the so colored layers were provided in a build box of a Voxeljet VTS 16-009. The build box was removed from the build-up device and provided in a uniaxial press. The powder in the build box was compressed at a pressure of about 100-300 MPa so that a blank of coherent powder was obtained. The blank was thermally debindered and then sintered at a 10 K/min rate up to 1450° C. with a dwell time of 120 min. As shown in FIG. 5 the color zones in the blank were delimited substantially sharp from each other.

Comparative Example

Figure 6:
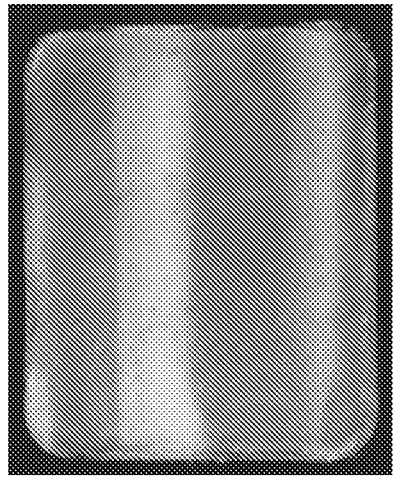

The Example was repeated in the same manner, but with the recoater operated to apply vibrations to the powder during dispensing. Accordingly the different color zones transitioned relatively smoothly between the individual zones. The result is shown in FIG. 6.

Materials

Exemplary powders as they may be used with the present invention are formed from a zirconia composition comprising:

Zr oxide calculated as ZrO2: from about 80 to about 97 wt.-%,
Al oxide calculated as Al2O3: from about 0 to about 0.15 wt.-%,
Y oxide oxide calculated as Y2O3: from about 1 to about 10 wt.-%,
Bi oxide calculated as Bi2O3: from about 0 to about 0.20 wt.-%,
Tb oxide calculated as Tb2O3: from about 0 to about 0.8 wt.-%, and optionally one or more of the following oxides:

Fe oxide calculated as Fe2O3: from about 0 wt.-% to about 0.15 wt.-%
Er oxide calculated as Er2O3: from about 0 wt.-% to about 1.0 wt.-%,
Mn oxide calculated as MnO2: from about 0 wt.-% to about 0.03 wt.-%,
organic binders: about 3 wt.-% to 5 wt.-%, wt.-% (percent by weight) with respect to the weight of the zirconia material.

The average grain size of the powder may be less than about 100 nm. The powders are preferably based on spray-dried powder granules containing organic binders to enable press-ability of the powder.

Result

It has been found that the present invention allows providing blanks having different color zones in a relatively efficient manner. Further it has been found that the present invention allows providing blanks in which the color zones transition smoothly between each other. Thus dental blanks and/or dental restorations can be formed which relatively pleasantly resemble the appearance of natural teeth.

Figure 7:
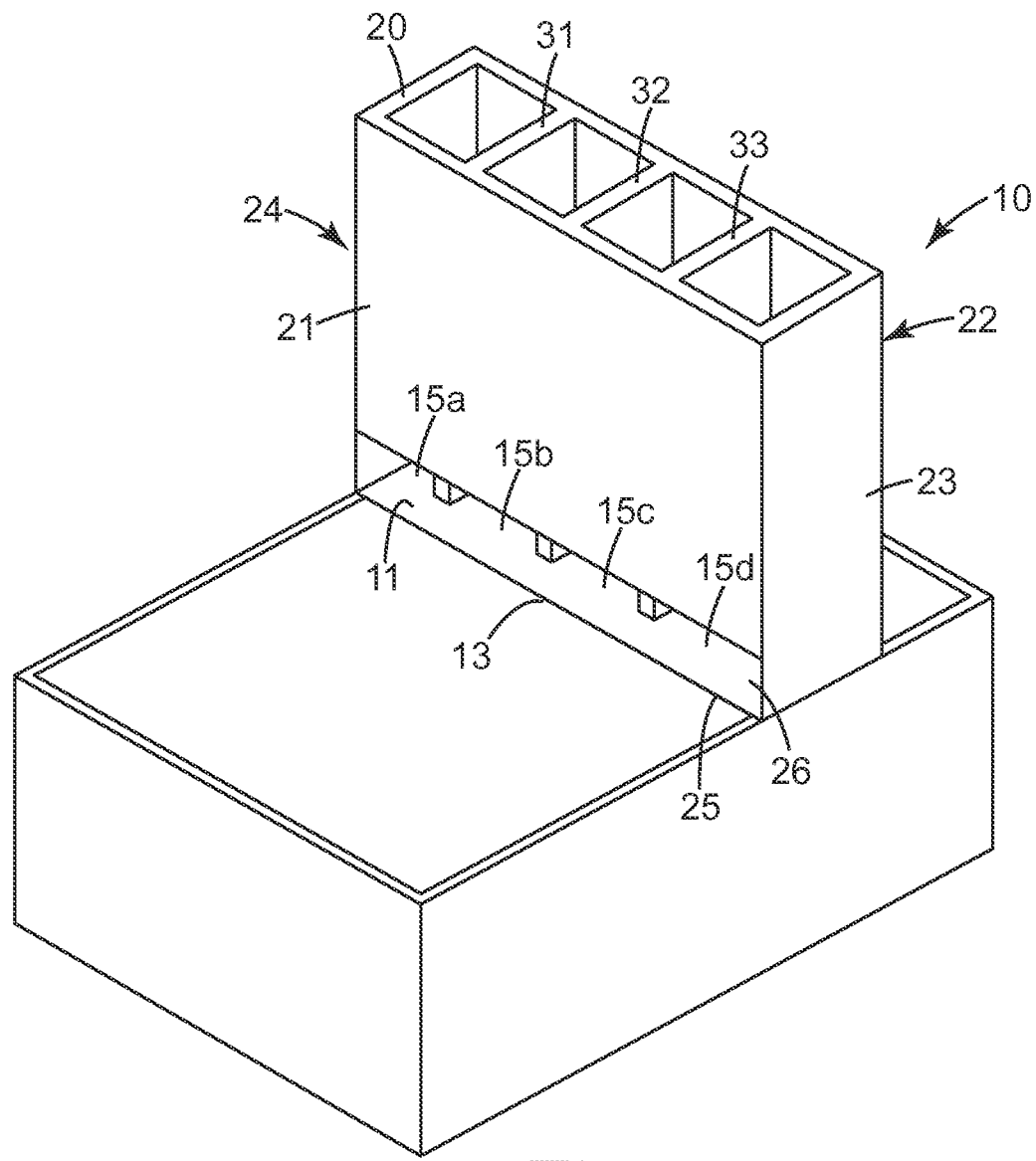
FIG. 7 is a perspective view of a device according to still a further embodiment of the invention.

FIG. 7 shows a recoater 10 which comprises a box 20 has a first, second, third and fourth outer side wall 21, 22, 23, 24 each extending generally vertical. The box 20 further has a bottom 25 wall which also forms the slide 11. The bottom wall 25 is in connection with the second, third, and fourth side wall 22, 23, 24. However the first side wall 21 and the bottom wall 25 are spaced from each other. In particular a slit 26 is formed between first side wall 21 and the bottom wall 25. The box 20 comprises three separation walls 31, 32, 33 which extend between the first side wall 21 and the opposite second side wall 22. Further the separation walls 31 are in connection with the bottom wall 25. The separation walls 31 are offset with respect to the dispensing edge 13 of the recoater 10. Thus a contiguous portion of the powder receiving surface 12 is arranged between the separation walls 31, 32, 33 and the dispensing edge 13. Outlet 15a is formed between the first outer side wall 21 of the box 20, the forth outer side wall 24, the separation walls 31 and the bottom wall 25. Outlet 15b is formed between the first outer side wall 21 of the box 20, the separation walls 31, 32 and the bottom wall 25. Outlet 15c is formed between the first outer side wall 21 of the box 20, the separation walls 32, 33 and the bottom wall 25. And outlet 15d is formed between the first outer side wall 21 of the box 20, the third outer side wall 23, the separation wall 33 and the bottom wall 25. As shown the outlets 15a, 15b, 15c and 15d also are offset from the dispensing edge 13 in a direction from the dispensing edge 13 toward the second outer side wall 22 of the box 20. The box 20 and the separation walls 31, 32, 33 form four powder supplies 14a, 14b, 14c, 14d opening in the outlets 15a, 15b, 15c, 15d, respectively. Accordingly the recoater 10 has four powder supplies 14a, 14b, 14c, 14d for individually supplying a first, a second, a third and a fourth powder on the slide 11, and is adapted such that the first, second, third and fourth powder can partially merge with each other on the contiguous portion of the powder receiving surface 12 between the outlets 15a, 15b, 15c, 15d.

The invention claimed is:

1. A device for powder based additive material manufacturing of dental appliances, comprising:
a build area and a recoater for providing a powder layer to the build area, the recoater comprising a slide and being adapted for dispensing of the powder to the build area, wherein the recoater has at least two powder supplies for individually supplying a first and a second powder on the slide and a powder transport section in which the first and second powder are brought in touch with each other for at least partially merging, wherein each powder supply has an outlet, and wherein the powder supply outlets are arranged adjacent each other, wherein the slide has a generally planar powder receiving surface terminating at one end in a dispensing edge and extending under the at least two powder supply outlets, wherein the device is adapted such that a vibration of the slide supports powder deposited on the powder receiving surface to slide toward the dispensing edge; wherein the slide receives the at least two powders side-by-side along a dimension parallel to the dispensing edge to form at least two corresponding powder tracks; wherein the at least two powder tracks partially merge at their lateral margins in a direction transverse to the direction of flow to form transition zones between the at least two powder tracks.

2. The device of claim 1, wherein the powder receiving surface further forms the powder transport section.

3. The device of claim 1, wherein outlets of the individual powder supplies are arranged essentially parallel to the powder receiving surface.

4. The device of claim 1, wherein the outlets of the powder supplies further are arranged along a first dimension generally parallel to the dispensing edge, or along a second dimension transverse to the dispensing edge, or along an angle between the first and second dimension.

5. The device of claim 1, wherein the outlets of the powder supplies further are juxtaposed along a generally regular zigzag line whose (imaginary) centerline extends generally parallel to the dispensing edge.

6. The device of claim 1, wherein the build area has a build platform exhibiting a generally planar build surface, the dispensing edge being arranged generally parallel to the build surface, and wherein the build platform and the slide are movable relative to each other in a dimension parallel to the build surface and a dimension perpendicular thereof.

7. The device of claim 1, wherein at least one or each of the powder supplies comprises a container for holding an amount of powder, wherein the container extends generally vertically and has a bottom end comprising the outlet in the form of an opening in the container.

8. The device of claim 7, wherein the opening extends in a dimension generally horizontally through a wall of the container.

9. The device of claim 1, wherein at least two of the powder supplies each comprise a powder, wherein the color of the powder in one of the powder supplies is different than the color of the powder in the other powder supply.

10. The device of claim 9, wherein the powder contains one or more elements to obtain optical effects like color and fluorescence selected from among Fe, Tb, Er, Mn, Bi, Th, Pr, Mn and combinations thereof.

11. The device of claim 1, wherein the powder supplies and the slide are mechanically coupled so as to enable transmission of vibrations between the slide and the powder supplies.

12. The device of claim 1, wherein the recoater comprises a box having a first, second, third and fourth outer side wall each extending generally vertical, a bottom wall which forms the slide and being in connection with the second, third, and fourth side wall, wherein the first side wall and the bottom wall are spaced from each other, and wherein the box further comprises at least one separation wall extending between the first side wall and the opposite second side wall and being in connection with the bottom wall.

13. The device of claim 1, further comprising: a vibration generator connected to the slide to induce the vibration of the slide.

14. The device of claim 13, the vibration generator comprising a motor-driven crank drive that converts a rotation into vibrations, the crank drive being based on an eccentrically rotationally driven shaft in which the rotation axis of the shaft is offset from the rotation axis, such that a velocity of the vibrations generated is determined by the offset and a frequency at which the shaft is rotated.

15. The device of claim 1, wherein the slide receives the at least two powders side-by-side along a dimension parallel to the dispensing edge.

16. The device of claim 1, wherein the at least two powder tracks partially merge at their margins laterally to a direction of flow as they slide toward the dispensing edge.

17. The device of claim 1, wherein a first one of the at least two powder tracks has a first tooth color, a second one of the at least two powder tracks has a second tooth color, and the transition zone between the first one of the at least two powder tracks and the second one of the at least two powder tracks having at least a third tooth color formed by a mixture of the first tooth color and the second tooth color.

\* \* \* \* \*